United States Patent [19]

Eichenberger et al.

[11] 4,264,599
[45] * Apr. 28, 1981

[54] PIPERIDINO-PROPANOLS

[75] Inventors: Kurt Eichenberger, Therwil; Hans Kühnis, Basel; Franz Ostermayer, Riehen; Herbert Schröter, Füllinsdorf, all of Switzerland

[73] Assignee: Ciba-Geigy Corporation, Ardsley, N.Y.

[ * ] Notice: The portion of the term of this patent subsequent to Mar. 13, 1996, has been disclaimed.

[21] Appl. No.: 921,521

[22] Filed: Jul. 3, 1978

[30] Foreign Application Priority Data

Jul. 8, 1977 [CH] Switzerland ............... 8483/77

[51] Int. Cl.³ ............... A61K 31/365; A61K 31/495; C07D 401/14
[52] U.S. Cl. ............... 424/250; 424/251; 544/295; 544/316; 544/318; 544/319; 544/336; 544/408; 544/409; 546/141; 546/153; 546/193; 546/201; 546/210; 546/309
[58] Field of Search ............... 544/295, 316, 336, 408, 544/409, 318, 319; 424/250, 267; 546/193, 210

[56] References Cited

U.S. PATENT DOCUMENTS

| | | | |
|---|---|---|---|
| 3,494,932 | 2/1970 | Brabander | 546/210 |
| 3,946,009 | 3/1976 | Wesson et al. | 544/408 |
| 3,956,335 | 5/1976 | Wilhelm et al. | 424/251 |
| 4,027,027 | 5/1977 | Jaeggi et al. | 544/408 |
| 4,038,279 | 7/1977 | Renth et al. | 544/318 |
| 4,075,208 | 2/1978 | Wilhelm et al. | 424/251 |
| 4,075,335 | 2/1978 | Wilhelm et al. | 424/251 |
| 4,115,575 | 9/1978 | Frei et al. | 544/408 |
| 4,134,983 | 1/1979 | Baldwin | 546/196 |
| 4,144,344 | 3/1979 | Eichenberger et al. | 546/210 |

Primary Examiner—Anton H. Sutto
Assistant Examiner—James H. Turnipseed
Attorney, Agent, or Firm—Prabodh I. Almaula

[57] ABSTRACT

The invention relates to novel piperidino-propanols, especially 1-(3-heterocyclyloxy-2-hydroxy-propanol)-4-(N-diazcyclyl)-piperidines of the formula

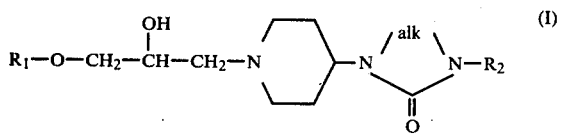

in which $R_1$ is a substituted or unsubstituted heteroaryl radical, $R_2$ is hydrogen or a substituted or unsubstituted aliphatic, cycloaliphatic, cycloaliphatic-aliphatic or araliphatic hydrocarbon radical or an acyl radical and alk is lower alkylene which separates the two nitrogen atoms from one another by 2 or 3 carbon atoms, or is a substituted or unsubstituted 1,2-phenylene radical, and salts thereof, as well as processes for their preparation, and also to pharmaceutical preparations containing these compounds and the use thereof, preferably in the form of pharmaceutical preparations as antihypertensive agents, antitachycardiac agents and α-sympathicolytic agents.

15 Claims, No Drawings

PIPERIDINO-PROPANOLS

The invention relates to novel piperidino-propanols, especially 1-(3-heterocyclyloxy-2-hydroxy-propanol)-4-(N-diazacyclyl)-piperidines of the formula

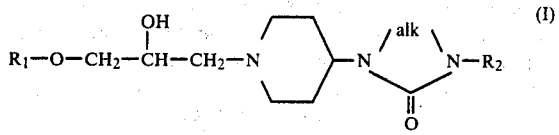

in which $R_1$ is a substituted or unsubstituted heteroaryl radical, $R_2$ is hydrogen or a substituted or unsubstituted aliphatic, cycloaliphatic, cycloaliphatic-aliphatic or araliphatic hydrocarbon radical or an acyl radical and alk is lower alkylene which separates the two nitrogen atoms from one another by 2 or 3 carbon atoms, or is a substituted or unsubstituted 1,2-phenylene radical, and salts thereof, as well as processes for their preparation, and also to pharmaceutical preparations containing these compounds and the use thereof, preferably in the form of pharmaceutical preparations.

A heteroaryl radical $R_1$ is a substituted or unsubstituted, preferably monocyclic, or bicyclic, heteroaryl radical, in particular an unsubstituted or substituted, for example monosubstituted, disubstituted or polysubstituted, preferably monocyclic azaaryl radical having 5 to 6 ring members and 1 to 2 ring nitrogen atoms, such as substituted or unsubstituted pyridyl, for example 2-, 3- or 4-pyridyl, imidazolyl, for example 2-imidazolyl, pyrimidinyl, for example 2- or 4-pyrimidinyl, pyridazinyl, for example 2-pyridazinyl, or pyrazinyl, for example 2-pyrazinyl, and also a substituted or unsubstituted bicyclic azaaryl radical, especially a benzoazaaryl radical, having 5 to 6 ring members and 1 to 2 ring nitrogen atoms in the azaaryl radical, such as substituted or unsubstituted indolyl, for example 4-indolyl, quinolinyl, for example 4-quinolinyl, or isoquinolinyl, for example 1-isoquinolinyl. Substituents of a heteroaryl radical are, inter alia, substituted or unsubstituted aliphatic or aromatic hydrocarbon radicals, free, etherified or esterified hydroxyl or mercapto, acyl, nitro or substituted or unsubstituted amino.

Substituted or unsubstituted aliphatic hydrocarbon radicals $R_2$ are corresponding lower alkyl, and also lower alkenyl or lower alkynyl, substituents, especially of lower alkyl, being in particular free, etherified or esterified hydroxyl or mercapto, acyl or substituted or unsubstituted amino.

Substituted or unsubstituted cycloaliphatic and cycloaliphatic-aliphatic hydrocarbon radicals $R_2$ are cycloalkyl, preferably having 3-8 and especially 5-7 ring carbon atoms, or cycloalkenyl, preferably having 5-8 and especially 6 to 7 ring carbon atoms, and also cycloalkyllower alkyl and cycloalkenyl-lower alkyl, in which cycloalkyl and cycloalkenyl are as defined above. Substituents of cycloaliphatic and cycloaliphatic-aliphatic hydrocarbon radicals are in particular substituted or unsubstituted aliphatic hydrocarbon radicals, free, etherified or esterified hydroxyl or oxo.

Araliphatic hydrocarbon radicals $R_2$ are in particular substituted or unsubstituted phenyl-lower alkyl, in which phenyl can contain, as substituents, for example substituted or unsubstituted aliphatic hydrocarbon radicals, free or etherified hydroxyl or mercapto, acyl, nitro or substituted or unsubstituted amino.

Substituted or unsubstituted aliphatic or aromatic hydrocarbon radicals as substituents of a heteroaryl radical $R_1$ or of cycloaliphatic, cycloaliphatic-aliphatic or araliphatic hydrocarbon radicals $R_2$ contain, inter alia, free, etherified or esterified hydroxyl groups or substituted or unsubstituted amino as substituents.

Etherified hydroxyl is in particular lower alkoxy or phenyl-lower alkoxy, and also lower alkenyloxy or lower alkynyloxy as well as hydroxy-lower alkoxy, lower alkoxy-lower alkoxy, lower alkylthio-lower alkoxy or lower alkanoyl-lower alkoxy, whilst esterified hydroxyl is in particular halogen, and also lower alkanoyloxy.

Etherified mercapto is in particular lower alkylthio, whilst esterified mercapto is, for examle, lower alkanoylthio.

Acyl is preferably the corresponding radical of an organic carboxylic acid and in particular is lower alkanoyl. Acyl is also the corresponding radical of a carbonic acid half-derivative, such as lower alkoxycarbonyl or substituted or unsubstituted carbamoyl. In the broadest sense of the definition, cyano is also an acyl radical.

Substituted or unsubstituted amino is acylamino, especially lower alkanoylamino or lower alkoxycarbonylamino, and also substituted or unsubstituted ureido. Substituted amino is also lower alkylamino or di-lower alkylamino, as well as lower alkyleneamino, lower oxaalkyleneamino or lower azaalkyleneamino, the aza nitrogen in the latter radical preferably being substituted, for example by lower alkyl.

Lower alkylene alk is preferably non-branched lower alkylene and in particular ethylene, as well as 1,3-propylene, but can also be branched lower alkylene, such as 1,2-propylene or 1,2- or 2,3-butylene.

If alk is a 1,2-phenylene radical, the latter can be substituted by lower alkyl, lower alkoxy or halogen.

In this specification the term "lower" used to qualify radicals and compounds denotes that these contain not more than 7, preferably not more than 4, carbon atoms.

Lower alkyl is, for example, methyl, ethyl, n-propyl, isopropyl, n-butyl, isobutyl or tert.-butyl; substituted lower alkyl is in particular corresponding methyl or 1- or 2-ethyl.

Lower alkenyl is, for example, vinyl, allyl, 2- or 3-methallyl or 3,3-dimethylallyl.

Lower alkynyl is especially propargyl.

Cycloalkyl is in particular cyclopentyl, cyclohexyl or cycloheptyl, and also cyclopropyl or cyclooctyl.

Cycloalkenyl is, for examle, 1- or 3-cyclohexenyl or 1-cycloheptenyl.

Cycloalkyl-lower alkyl is, for example, cyclopentylmethyl, cyclohexylmethyl, 2-cyclohexylethyl or cycloheptylmethyl.

Cycloalkenyl-lower alkyl is, for example, 1-cyclohexenylmethyl, 2-(1-cyclohexenyl)-ethyl or 1-cycloheptenylmethyl.

Phenyl-lower alkyl is, inter alia, benzyl, 1- or 2-phenylethyl or 3-phenylpropyl.

Lower alkoxy is, for example, methoxy, ethoxy, n-propoxy, isopropoxy, n-butoxy or isobutoxy.

Phenyl-lower alkoxy is, for example, benzyloxy or 1- or 2-phenylethoxy.

Hydroxy-lower alkoxy, for example, 2-hydroxyethoxy and also 2- or 3-hydroxypropoxy.

Lower alkoxy-lower alkoxy is, inter alia, lower alkoxy-methoxy or 1- and especially 2-lower alkoxy-ethoxy, for example methoxy-methoxy, 2-methoxy-ethoxy or 2-ethoxy-ethoxy.

Lower alkylthio-lower alkoxy is especially lower alkylthiomethoxy or 1- and in particular 2-lower alkylthio-ethoxy, for example 2-methylthio-ethoxy or 2-ethylthio-ethoxy.

Lower alkanoyl-lower alkoxy is especially acetonyloxy.

Lower alkenyloxy is, for example, allyloxy, 2- or 3-methallyloxy or 3,3-dimethylallyloxy.

Lower alkynyloxy is especially propargyloxy.

Halogen is preferably halogen with an atomic number of not more than 35, i.e. fluorine, chlorine or bromine.

Lower alkanoyloxy is, for examle, acetoxy, propionyloxy or pivaloyloxy.

Lower alkylthio is, for example, methylthio, ethylthio, n-propylthio or isopropylthio.

Lower alkanoylthio is, inter alia, acetylthio or propionylthio.

Lower alkanoyl is, for example, acetyl, propionyl or butyryl.

Lower alkoxycarbonyl is, for example, methoxycarbonyl or ethoxycarbonyl.

Substituted or unsubstituted carbamoyl is, for example, carbamoyl or N-lower alkyl- or N,N-di-lower alkylcarbamoyl, such as N-methyl-carbamoyl, N,N-dimethylcarbamoyl, N-ethylcarbamoyl or N,N-diethylcarbamoyl.

Lower alkanoylamino is, for example, acetylamino or propionylamino.

Lower alkoxycarbonylamino is, for example, methoxycarbonylamino or ethoxycarbonylamino.

Substituted or unsubstituted ureido is, for example, ureido or 3-lower alkylureido or 3-cycloalkylureido, in which cycloalkyl has, for example, 5–7 ring members, for example 3-methylureido, 3-ethylureido or 3-cyclohexylureido.

N-Lower alkylamino and N,N-di-lower alkylamino are, for example, methylamino, ethylamino, dimethylamino or diethylamino.

Lower alkyleneamino preferably contains 5–7 ring carbon atoms and is, for example, pyrrolidino or piperidino.

Lower oxaalkyleneamino is in particular morpholino, whilst lower azaalkyleneamino is in particular corresponding N-lower alkyl-lower azaalkyleneamino, for example 4-methyl-1-piperazino.

Substituted lower alkyl groups are, for example, hydroxy-lower alkyl, lower alkoxy-lower alkyl, halogeno-lower alkyl, lower aklanoylamino-lower alkyl or lower alkoxycarbonylamino-lower alkyl.

Hydroxy-lower alkyl is preferably hydroxymethyl or 1- and in particular 2-hydroxyethyl.

Lower alkoxy-lower alkyl is preferably lower alkoxymethyl or 1-and in particular 2-lower alkoxyethyl, for example methoxymethyl, ethoxymethyl, 2-methoxyethyl or 2-ethoxy-ethyl.

Halogeno-lower alkyl is preferably halogenomethyl, for example trifluoromethyl.

Lower alkanoylamino-lower alkyl is especially lower alkanoylaminomethyl or 1- and in particular 2-lower alkanoylamino-ethyl, for example acetylamino-methyl, 2-acetylamino-ethyl or 2-propionylamino-ethyl.

Lower alkoxycarbonylamino-lower alkyl is especially lower alkoxycarbonylaminomethyl or 1- and in particular 2-lower alkoxycarbonylamino-ethyl, for example methoxycarbonylaminomethyl, 2-methoxycarbonylamino-ethyl or 2-ethoxycarbonylamino-ethyl.

The novel compounds can be in the form of their salts, such as their acid addition salts and in particular their pharmaceutically usable, non-toxic acid addition salts. Suitable salts are, for example, those with inorganic acids, such as hydrogen halide acids, for example hydrochloric acid or hydrobromic acid, sulphuric acids, for example sulphuric acid, or phosphoric acids, or with organic acids, such as aliphatic, cycloaliphatic, aromatic or heterocyclic carboxylic or sulphonic acids, for example formic acid, acetic acid, propionic acid, succinic acid, glycollic acid, lactic acid, malic acid, tartaric acid, citric acid, ascorbic acid, maleic acid, hydroxymaleic acid, pyruvic acid, fumaric acid, benzoic acid, 4-aminobenzoic acid, anthranilic acid, 4-hydroxybenzoic acid, salicylic acid, 4-aminosalicylic acid, embonic acid, methanesulphonic acid, ethanesulphonic acid, 2-hydroxyethanesulphonic acid, ethylenesulphonic acid, toluenesulphonic acid, naphthalenesulphonic acid or sulphanilic acid.

The novel compounds of the present invention can be in the form of mixtures of isomers, such as racemates, or of pure isomers, for example optically active antipodes.

The novel compounds have valuable pharmacological properties. Thus, they have a hypotensive action, as can be shown in animal experiments, for example on intravenous administration in doses of about 0.1 to about 30 mg/kg to narcotised cats. In addition, the novel compounds effect antitachycardia, as can also be shown in animal experiments, for example in in vitro experiments in concentrations of about 1 to about 100 γ/ml on guineapig hearts (Langendorff preparation), and an α-sympathicolysis, for example in in vitro experiments at concentrations of about 0.01 to about 10 γ/ml on rats (isolated perfused mesenteric artery preparation; in accordance with a modification of the method of McGregor, J. Physiol., Volume 177, page 21 (1965)). The novel compounds can therefore be used as antihypertensive agents, antitachycardiac agents and α-sympathicolytic agents. Furthermore, the novel compounds can be used as starting materials or intermediates for the preparation of other compounds, especially compounds having a therapeutic action.

The invention relates in particular to compounds of the formula I in which $R_1$ is substituted or unsubstituted monocyclic heteroaryl or benzoheteroaryl having 5 to 6 ring members and 1 to 2 ring nitrogen atoms in the radical $R_1$, substituents of the heterocyclic aryl radical being substituted or unsubstituted lower alkyl, for example lower alkyl, lower alkoxy-lower alkyl, lower alkanoylamino-lower alkyl or lower alkoxycarbonylaminolower alkyl, or unsubstituted or correspondingly substituted phenyl, or free, etherified or esterified hydroxyl or mercapto, for example lower alkoxy, lower alkoxy-lower alkoxy, lower alkylthio-lower alkoxy, lower alkylthio or halogen, and/or nitro, $R_2$ is hydrogen or substituted or unsubstituted lower alkyl, cycloalkyl, cycloalkyl-lower alkyl or phenyl-lower alkyl, substituents of these radicals being, for example, substituted or unsubstituted lower alkyl, for example lower alkyl, or free, etherified or esterified hydroxyl or mercapto, for example lower alkoxy, lower alkylthio and/or halogen, or, furthermore, is lower alkanoyl or lower alkoxycarbonyl, and alk is as defined above, and salts, especially acid addition salts and in particular pharmaceutically usable, non-toxic acid addition salts thereof.

The invention relates especially to compounds of the formula I in which $R_1$ is monocyclic monoazaaryl or diazaaryl having six ring members, which is unsubstituted or substituted by lower alkyl, for example methyl, lower alkoxy, for examle methoxy, lower alkylthio, for example methylthio or ethylthio, halogen with an atomic number of not more than 35, for examle chlorine or bromine, and/or nitro, such as pyridyl, for examle 2-, 3- or 4-pyridyl, pyrimidinyl, for example 2- or 4-pyrimidinyl, pyrazinyl, for example 2-pyrazinyl, or indolyl, for example 4-indolyl, $R_2$ is hydrogen, lower alkyl, for example methyl, ethyl or isopropyl, cycloalkyl, for example cyclopentyl, or phenyl-lower alkyl which is unsubstituted or substituted in the phenyl moiety by lower alkyl, for example methyl, lower alkoxy, for example methoxy, and/or halogen with an atomic number of not more than 35, for example chlorine or bromine, for example benzyl or 1- or 2- phenylethyl, and alk is lower alkylene having 2-3 carbon atoms, which separates the two nitrogen atoms by 2-3 carbon atoms, for examle ethylene or 1,3-propylene, and salts, especially acid addition salts and in particular pharmaceutically usable non-toxic acid addition salts thereof.

The invention relates especially to compounds of the formula I in which $R_1$ is 2-pyrazinyl which is unsubstituted or substituted by lower alkyl, for example by methyl, lower alkoxy, for example methoxy, lower alkylthio, for example methylthio or ethylthio, halogen with an atomic number of not more than 35, for example chlorine or bromine, and/or nitro, and also is unsubstituted or correspondingly substituted pyridyl, for example 2- or 3-pyridyl, in which substituents can assume any position, but at least one substituent preferably assumes the ortho-position relative to the linking ring carbon atom and/or nitrogen atom of the heteroaryl radical, and also 4-indolyl, and $R_2$ is hydrogen, lower alkyl, for example methyl, ethyl or isopropyl, or phenyl-lower alkyl, for example benzyl or 1- or 2-phenylethyl, and alk is lower alkylene having 2-3 carbon atoms, which separates the two nitrogen atoms by 2-3 carbon atoms, for example ethylene or 1,3-propylene, and salts, especially acid addition salts and in particular pharmaceutically usable non-toxic acid addition salts thereof.

The invention relates in particular to compounds of the formula I in which $R_1$ is 2-pyrazinyl and also is pyridyl, for example 2- or 3-pyridyl, and 4-indolyl, which in the ortho-position relative to the linking carbon atom and/or nitrogen atom preferably is substituted by lower alkyl, for example methyl, lower alkoxy, for example methoxy, lower alkylthio, for example methylthio or ethylthio, halogen with an atomic number of not more than 35, for example chlorine or bromine, or nitro, and which, if desired, can contain further substituents of this type, $R_2$ is especially hydrogen and also lower alkyl, for example methyl, or phenyl-lower alkyl, for example benzyl, and alk is ethylene, and salts, especially acid addition salts and in particular pharmaceutically usable non-toxic acid addition salts thereof.

The invention relates in particular to compounds of the formula I in which $R_1$ is 4-indolyl, 2-pyrazinyl or pyridyl, which in the ortho-position relative to the linking carbon atom and/or nitrogen atom preferably is substituted by lower alkyl, for example methyl, lower alkoxy, for example methoxy, lower alkylthio, for example methylthio or ethylthio, halogen with an atomic number of not more than 35, for example chlorine or bromine, or nitro, $R_2$ is hydrogen and also lower alkyl, for example methyl, and alk is ethylene, and salts, especially acid addition salts and in particular pharmaceutically usable non-toxic acid addition salts thereof.

The invention relates in particular to the compounds described in the examples, especially those compounds of the formula I which contain, as the radical $R_1$, a preferably substituted 2-pyrazinyl radical.

The novel compounds are obtained by methods known per se. Thus, it is possible, for example, to react a compound of the formula

$$R_1-O-X_1 \tag{II}$$

or a salt thereof, with a compound of the formula

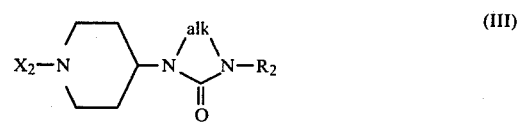

(III)

or a salt thereof, in which formulae one of the radicals $X_1$ and $X_2$ is hydrogen and the other is the radical of the formula

$$-CH_2-CH-CH_2-X_4 \quad\text{with } X_3 \tag{IV}$$

in which $X_3$ is a free hydroxyl group and $X_4$ is a reactive esterified hydroxyl group, or in whch $X_3$ and $X_4$ together form an epoxy group, and, if desired, to convert an obtainable compound into another compound of the formula I and/or, if desired, to convert an obtainable free compound into a salt and/or, if desired, to convert an obtainable salt into the free compound or into another salt and/or , if desired, to separate an obtainable mixture of isomers into the isomers.

Thus, the above reaction can be carried out, for example, by reacting a compound of the formula

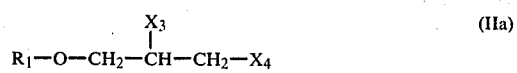

(IIa)

with a compound of the formula

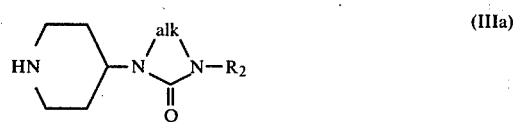

(IIIa)

or a salt thereof, or by reacting a compound of the formula $R_1$—OH (IIIb) or a salt thereof with a compound of the formula

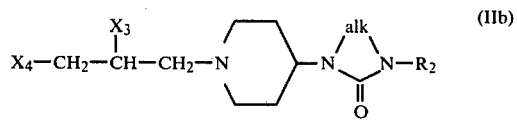

(IIb)

in which formulae either $X_3$ is free hydroxyl and $X_4$ is a reactive esterified hydroxyl group or $X_3$ and $X_4$ together form an epoxy group.

A reactive esterified hydroxyl group $X_4$ is a hydroxyl group esterified by a strong inorganic or organic acid, in particular a hydrogen halide acid, for example hydrochloric acid, hydrobromic acid or hydriodic acid, and also sulphuric acid, or by an organic sulphonic acid, such as an aromatic sulphonic acid, for example benzene-sulphonic acid, 4-bromobenzenesulphonic acid or 4-toluenesulphonic acid. Thus, $X_4$ is in particular chlorine or bromine, and also iodine, if it does not form an opoxy grouping together with $X_3$.

The above reaction is carried out in a conventional manner. When the starting material of the formula IIa which is used is a reactive ester, the reaction is preferably carried out in the presence of a basic condensing agent and/or with an excess of the basic compound of the formula IIIa.

If the starting material used is a reactive ester of the formula IIb, the compound of the formula IIIb is preferably employed in the form of a salt, such as a metal salt, especially an alkali metal salt, for example the sodium or potassium salt, or the reaction is carried out in the presence of an acid-binding agent, especially a condensing agent, which is able to form a salt with the compound of the formula IIIb, such as an alkali metal lower alkoxide.

The above reaction is carried out in the absence or preferably in the presence of a solvent or diluent, usually an inert solvent or diluent, and if necessary with cooling or warming, for example in a temperature range from about 0° C. to about 150° C., in a closed vessel and/or in an inert gas atmosphere, for example a nitrogen atmosphere.

The starting materials are known or can be obtained in a manner known per se. Thus, it is possible, for example, to react piperidin-4-one in which the secondary amino group can, if desired, be protected in a manner known per se, for example by a benzyl radical or an easily detachable acyl radical, with a diamine of the formula $H_2N$-alk-$HN$-$R_2$ (V) and, at the same time or subsequently, to treat the reaction product with a suitable reducing agent, such as catalytically activated hydrogen or a hydride reducing agent, for example sodium cyanoborohydride. In the intermediate thus obtainable, the 2-oxo-1,3-diazacycloalkane radical is formed, for example, by treatment with a suitable reactive carbonic acid derivative, such as a di-lower alkyl carbonate or phosgene; if necessary, a N-protective group can be replaced by hydrogen in a manner known per se. A starting material of the formula IIIa which is thus obtainable can be converted to a starting material of the formula IIb in a manner known per se, for example by treatment with a reactive ester of a 2,3-epoxy-1-propanol, such as a 2,3-epoxy-1-propyl halide, and, if desired, by subsequent reaction with a strong acid, such as a hydrogen halide acid.

The novel compounds can also be obtained by converting $X_5$ in a compound of the formula

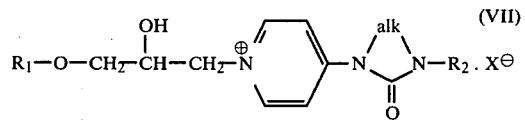

in which $X_5$ is a radical which can be converted to hydroxyl, to hydroxyl and, if desired, carrying out the additional process steps.

In a starting material of the formula VI, $X_5$ is especially an esterified hydroxyl group and in particular acyloxy, in which acyl is the corresponding radical of an organic carboxylic acid, such as a lower alkanecarboxylic acid, for example acetyl, propionyl or pivaloyl, or of an aromatic carboxylic acid, for example benzoyl.

The conversion of $X_5$ to hydroxyl can be carried out by means of solvolysis, especially by hydrolysis, in which case the reaction can be carried out with water in an alkaline or acid medium, or by alcoholysis (transesterification), in which case the reaction is carried out, for example, with a lower alkanol, for example methanol or ethanol, if appropriate in the presence of a transesterification catalyst, such as an alkali metal lower alkanolate, for example sodium methanolate, ethanolate or butanolate or potassium methanolate, ethanolate or butanolate. The reaction is carried out in the absence or presence of solvents or diluents and, if necessary, with cooling or warming, for example in a temperature range from about 0° C. to about 120° C., in a closed vessel and/or in an inert gas atmosphere.

The starting materials of the formula VI can be obtained, for example, by converting $X_3$ in a compound of the formula IIa, in which $X_3$ is hydroxyl and $X_4$ is a reactive esterified hydroxyl group, into an esterified hydroxyl group which can be converted to hydroxyl, for example to acyloxy by acylating with a reactive derivative, such as an anhydride, which can be a mixed anhydride, of an organic carboxylic acid, and reacting the intermediate thus obtainable, preferably in excess, with a compound of the formula IIIa.

The novel compounds can also be obtained by reducing the pyridinium ring in a compound of the formula

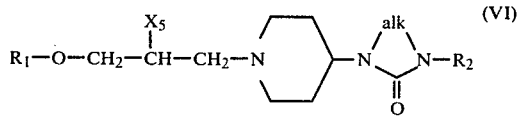

in which $X^\ominus$ is an anion, to the piperidine ring and, if desired, carrying out the additional process steps.

An anion $X^\ominus$ is especially that of an acid, preferably of a mineral acid, such as a hydrogen halide acid, for example hydrochloric acid or hydrobromic acid, or of a suitable organic carboxylic or sulphonic acid.

The above reduction can be carried out in a conventional manner, preferably by means of catalytic hydrogenation, such as with hydrogen in the presence of a suitable hydrogenation catalyst, for example of a heavy metal catalyst, for example a palladium, platinum or Raney nickel catalyst, or by treatment with nascent hydrogen, such as by treatment with an alkali metal, for example sodium or potassium, in the presence of an alcohol, such as a lower alkanol, for example ethanol or n-butanol.

The reduction, with which care must be taken that other reducible groups are not attacked, can also be carried out step-wise, since partially saturated pyridine compounds, for example 1,2,5,6-tetrahydro-pyridine compounds can be formed as intermediates and on treatment with the same reducing agent, if desired under different conditions, or with another reducing agent, these can be converted to the desired piperidine compounds.

The above reaction is carried out in the absence and especially in the presence of a solvent or diluent and, if necessary, with cooling or warming, for example in a temperature range from about 0° C. to about 120° C., in a closed vessel and/or in an inert gas atmosphere.

The starting materials can be prepared in a manner known per se, by, for example, reacting 4-amino-pyridine with a compound of the formula $Hal_1$-$alk_o$—C(=O)—NH-$R_2$ (VIII), in which latter formula $alk_o$ is the lower alkylene radical shortened by one chain carbon atom; this compound is obtained, for example, by treating an amino compound of the formula $H_2N-R_2$ (IX) with an acid halide of the formula $Hal_1-alk_o-C(=O)-Hal_2$ (X), in which $Hal_1$ and $Hal_2$ are each halogen, for example chlorine. In the intermediate of the formula

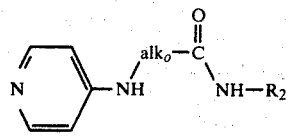
(XI)

which is thus formed, the carbonyl group is reduced to the methylene group, for example by treatment with lithium aluminum hydride, and the 2-oxo-1,3-diazacycloalkane ring is formed, for example by treatment with phosgene. The 4-(2-oxo-3-$R_2$-1,3-diazacycloalkyl-1-yl)-pyridine compound thus obtainable is then reacted with a compound of the formula IIa in which $X_3$ is hydroxyl and $X_4$ is a reactive esterified hydroxyl group, especially halogen.

The novel compounds of the formula I can also be obtained by forming the 2-oxo-1,3-diazacycloalkane ring in a compound of the formula

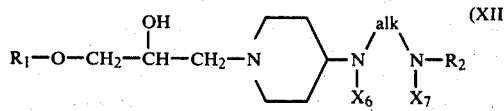
(XII)

in which one of the radicals $X_6$ and $X_7$ is hydrogen and the other is the acyl radical of a carbonic acid half-derivative, by cyclisation and, if desired, carrying out the additional process steps.

In a starting material of the formula XII, the acyl radical of a carbonic acid half-derivative is the corresponding radical of a carbonic acid half-ester, such as lower alkoxycarbonyl, for example methoxycarbonyl or ethoxycarbonyl, of a carbonic acid half-halide, i.e. halogenocarbonyl, for example chlorocarbonyl or bromocarbonyl, or of a carbonic acid half-amide, for example carbamoyl.

The cyclisation is carried out in the absence or presence of a solvent or diluent and, if necessary, in the presence of a condensing agent, preferably a basic condensing agent such as of an alkali metal hydroxide, carbonate, bicarbonate or lower alkanoate or alkaline earth metal hydroxide, carbonate, bicarbonate or lower alkanoate, and also of an organic base, such as a tertiary amine or a base of the pyridine type, with cooling or, preferably, warming, for example in a temperature range from about $+20°$ C. to about $150°$ C., in a closed vessel and/or in an inert gas atmosphere.

The starting material of the formula XII is prepared by methods known per se and preferably in situ by reacting a compound of the formula XII in which $X_6$ and $X_7$ are hydrogen with a reactive derivative of carbonic acid. Reactive derivatives of carbonic acid are corresponding esters, such as a di-lower alkyl carbonate, for example diethyl carbonate, or halides, for example phosgene, and also amides, for example urea or carbonyldiimidazole, and also halogenocarbonic acid esters, such as lower alkyl chlorocarbonates, for example isobutyl chlorocarbonate, or carbamic acid halides, for example cabamic acid chloride.

The reaction is carried out in a conventional manner, usually in the presence of an inert solvent, preferably of an aliphatic or aromatic hydrocarbon, which can be halogenated, for example chloroform or toluene, or also of an amide or nitrile, for example dimethylformamide, dimethylacetamide or acetonitrile, or of a cycloaliphatic ether, such as dioxan and tetrahydrofuran. The reaction is preferably carried out in the presence of a condensing agent, especially of a basic condensing agent, such as of an alkali metal hydroxide, carbonate or bicarbonate or alkaline earth metal hydroxide, carbonate or bicarbonate, for example sodium hydroxide or potassium hydroxide, sodium carbonate or bicarbonate or potassium carbonate or bicarbonate, or of an alkali metal lower alkanoate, for example sodium acetate, or of an alkali metal lower alkanolate, for example sodium methanolate or potassium tert.-butanolate, or of an organic tertiary nitrogen base, such as of a tri-lower alkylamine, for example trimethylamine or triethylamine, or pyridine.

A compound of the formula XII in which $X_6$ and $X_7$ are hydrogen can be obtained, for example, by reacting piperidin-4-one with a compound of the formula IIa in which $X_3$ is hydroxyl and $X_4$ is a reactive esterified hydroxyl group, especially halogen, and then allowing the intermediate to react with a diamine of the formula V and, at the same time or subsequently, carrying out the treatment with a reducing agent, such as catalytically activated hydrogen or a suitable hydride reducing agent, for example sodium cyanoborohydride.

The novel compounds of the formula I can also be obtained by converting $X_8$ in a compound of the formula

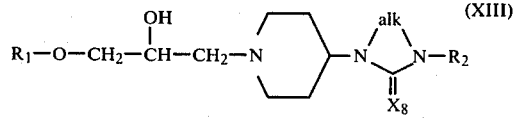
(XIII)

in which $X_8$ is an imino radical which can be converted to oxo, into oxo and, if desired, carrying out the additional process steps.

The imino radical $X_8$ can be substituted, for example by lower alkyl or phenyl. A corresponding starting material of the formula XIII can be converted to the corresponding compound of the formula I by hydrolysis, preferably in the presence of an acid agent, such as of a mineral acid, for example hydrochloric acid.

The above reaction is carried out in the absence or preferably in the presence of a solvent or diluent and, if necessary, with cooling or warming, for example in a temperature range from about $0°$ C. to about $150°$ C., if necessary in a closed vessel and/or in an inert gas atmosphere.

The starting materials of the formula XIII can be obtained in a manner known per se, for example by treating a compound of the formula XII, in which each of the radicals $X_6$ and $X_7$ is hydrogen, with a cyanogen halide, for example cyanogen bromide, preferably in the presence of a suitable condensing agent, for example a basic condensing agent, with simultaneous or subsequent cyclisation to the 2-imino-1,3-diazacycloalkane ring of the starting material of the formula XIII.

In resulting compounds it is possible, within the scope of the end products, to detach, introduce or modify substituents in a manner known per se.

Thus, in compounds of the formula I containing unsaturated substituents, for example lower alkenyl, lower alkenyloxy or lower alkynyloxy, these can be reduced by suitable reduction methods to give corresponding saturated compounds or, in the case of substituents containing a triple bond, to give a compound containing a double bond. The reducing agent used is preferably catalytically activated hydrogen.. A suitable catalyst is in particular the Lindlar catalyst (Pd-Pb-CaCO$_3$).

It is also possible, in a resulting compound of the formula I which contains halogen, such as bromine or iodine, as a substituent of an aromatic radical, to replace this halogen by trifluoromethyl, for example by treatment with trifluoromethyl iodide in the presence of copper powder and of a suitable aprotic solvent, such as pyridine, dimethylformamide or acetonitrile.

In a resulting compound of the formula I, an α-phenyl-lower alkyl group, for example in benzyloxy, can be detached by treating the corresponding compound with catalytically activated hydrogen and replaced by hydrogen, for example a benzyloxy group can be replaced by hydroxyl.

Furthermore, in a compound of the formula I which contains hydroxyl or mercapto in the form of a primary carbinol group or of a phenolic hydroxyl group as a substituent, this, which can be in the form of a salt, for example in the form of an alkali metal salt, can be converted to etherified hydroxyl or mercapto, for example lower alkoxy or lower alkylthio, by treatment with a reactive ester of an alcohol, such as a substituted or unsubstituted lower alkyl halide. In addition, hydroxyl in a hydroxy-lower alkyl or hydroxy-lower alkoxy substituent, usually in the form of a reactive esterified hydroxyl group, such as halogen, for example chlorine, can be reacted with an alcohol, for example a lower alkanol, or a mercaptan, for example a lower alkymercaptan, preferably in the presence of a basic agent which is able, for example, to convert an alcohol or a mercaptan into a metal compound, and compounds of the formula I can thus be obtained which contain correspondingly etherified hydroxy-or mercapto-lower alkyl or -lower alkoxy. Furthermore, in a resulting compound, a reactive esterified hydroxyl group, such as halogen, for example chlorine, especially in the α-position relative to a ring nitrogen atom in a radical R$_1$, can be converted to an etherified or esterified hydroxyl or mercapto group, for example to lower alkoxy or lower alkylthio, by treatment with an alcoholate or thiolate compound, such as an alkali metal lower alkanolate or thio-lower alkanolate, for example a sodium or potassium lower alkanolate or thio-lower alkanolate.

In a compound of the formula I, a propargyloxy group can be converted to the acetonyloxy group, for example by hydration in an acid medium and in the presence of a mercury-II salt, for example by treatment with an aqueous mineral acid, for example dilute hydrochloric or sulphuric acid, in the presence of mercury-II chloride.

Furthermore, in a compound of the formula I which contains esterified carboxyl or lower alkoxycarbonylamino as a substituent, this can be converted to amidated carboxyl or, if desired, ureido by treatment with ammonia or an amine, preferably with an excess thereof and at elevated temperature.

In a compound of the formula I which contains primary amino as a substituent, the latter can also be substituted; thus, amino can be acylated, for example by treating the amino compound with a suitable acid derivative, such as an anhydride, which can be mixed, for example a corresponding chloride, if necessary in the presence of a basic agent.

The reactions described above can, if desired, be carried out at the same time or successively and in any order and in a conventional manner, for example in the presence or absence of solvents or diluents, if necessary in the presence of condensing agents and/or catalytic agents, with cooling or warming, in a closed vessel and/or in an inert gas atmosphere.

Depending on the process conditions and starting materials, the end products are obtained in the free form or in the form of their salts, especially their acid addition salts: the said salts also fall within the scope of the invention. Resulting salts can be converted to the free compounds in a manner known per se, acid addition salts, for example, by treatment with basic agents, including suitable ion exchangers. On the other hand, resulting free compounds can form salts, for example by treatment with organic or inorganic acids. Furthermore, resulting salts can be converted to other salts, acid addition salts, for example, by treatment with suitable heavy metal salts or anion exchangers.

The abovementioned salts or other salts of the novel compounds of the formula I, for example the picrates can also be used to purify the resulting free bases, by converting the free bases to salts, separating these off and again liberating the bases from the salts. Because of the close relationships between the novel compounds in the free form and in the form of their salts, what is stated in this specification in respect of the free compounds also applies by analogy to the corresponding salts.

Depending on the choice of starting materials and procedures, the novel compounds can be in the form of the racemates or of the optical antipodes.

Resulting racemates can be resolved into the optical antipodes by known methods, for example by recyrstallisation from an optically active solvent, with the aid of micro-organisms or by reaction with an optically active acid which forms salts with the racemic compound and separation of the salts obtained in this way, for example on the basis of their different solubilities, into the diasteromeric salts, from which the free antipodes can be liberated by the action of suitable agents. Particularly suitable optically active acids are, for example, the D- and L-forms of tartaric acid, di-toluyl-tartaric acid, malic acid, mandelic acid, camphorsulphonic acid or quinic acid.

The invention also relates to those embodiments of the process in which a compound obtainable as an intermediate at any stage of the process is used as the starting material and the missing process steps are carried out, of the process is discontinued at any stage, or in which a starting material is formed under the reaction conditions, or in which a reactant is, if desired, in the form of a derivative, for example of a salt.

The starting materials used for carrying out the reactions according to the invention are preferably those which result in the groups of end products mentioned in particular initially and especially in the end products specifically described or singled out.

The novel compounds can be used, for example, in the form of pharmaceutical preparations which contain a pharmacologically effective amount of the active ingredient if desired together with inorganic or organic, solid or liquid, pharmaceutically usable carriers which are suitable for enteral, for example oral, or parenteral administration. Thus, tablets or gelatin capsules are used which contain the active ingredient together with diluents, for example lactose, dextrose, sucrose, mannitol, sorbitol, cellulose and/or glycine, and/or lubricants, for example silica, talc, stearic acid or salts thereof, such as magnesium stearate or calcium stearate, and/or polyethylene glycol. Tablets can also contain binders, for example magnesium aluminium silicate, starches, such as maize starch, corn starch, rice starch or arrowroot, gelatin, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. Furthermore, the novel pharmacologically active compounds can be used in the form of preparations which can be administered parenterally or of infusion solutions. Such solutions are preferably isotonic aqueous solutions or suspensions and, for example in the case of lyophilised preparations which contain the active ingredient on its own or together with a carrier material, for example mannitol, these can be prepared before use. The pharmaceutical preparations can be sterilised and/or contain adjuncts, for example preservatives, stabilisers, wetting agents and/or emulsifiers, solubilising agents, salts for regulating the osmotic pressure and/or buffers. The pharmaceutical preparations of the specification, which, if desired, can contain further pharmacologically active substances, are prepared in a manner known per se, for example by means of conventional mixing, granulating, sugar-coating, dissolving or lyophilising methods, and contain from about 0.1% to 100%, especially from about 1% to about 50% of the active ingredient; lyophilisates contain up to 100% of the active ingredient.

The dosage can depend on various factors, such as the mode of application, the species, the age and/or the individual condition. The doses to be administered daily are between about 5 mg and about 50 mg in the case of oral administration to warm-blooded animals weighing about 70 kg.

The following examples illustrate the invention; temperatures are in degrees centigrade.

EXAMPLE 1

A mixture of 22.5 g of crude 3-(2,3-epoxypropoxy)-2-methoxy-pyridine and 21.0 g of 1-(4-piperidyl)imidazolidin-2-one in 250 ml of isopropanol is refluxed for 14 hours. The reaction mixture is evaporated and the residue is dissolved in ethyl acetate and extracted with 2 N hydrochloric acid. The acid extract is rendered alkaline with a concentrated aqueous solution of sodium hydroxide and extracted with ethyl acetate. The organic solution is evaporated and the residue is recrystallised from a mixture of methylene chloride and diethyl ether. The 1-{1-[2-hydroxy-3-(2-methoxy-3-pyridyloxy)-propyl]-4-piperidyl}-imidazolidin-2-one thus obtained melts at 132°–134°.

The starting material can be obtained as follows:

A mixture of 15.4 g of 3-hydroxy-2-methoxy-pyridine, 16 g of potassium carbonate, 25 ml of epichlorohydrin and 150 ml of acetonitrile is refluxed for 7 hours. Cooling and filtering the mixture and evaporating the filtrate yields crude 3-(2,3-epoxy-propoxy)-2-methoxypyridine, which is used without further purification.

In an analogous manner, 1-{1-[2-hydroxy-3-(2-methoxy-6-methyl-3-pyridyloxy)-propyl]-4-piperidyl}-imidazolidin-2-one, which after recrystallisation from a mixture of methylene chloride and diethyl ether melts at 144°–147°, can be obtained by reacting 20 g of crude 3-(2,3-epoxy-propoxy)-2-methoxy-6-methyl-pyridine and 16.5 g of 1-(4-piperidyl)-imidazolidin-2-one. The starting material can be obtained analogously to the process described above from 3-hydroxy-2-methoxy-6-methylpyridine and is reacted without further purification.

EXAMPLE 2

A solution of 25.0 g of 2-(2,3-epoxy-propoxy)-3-methoxy-pyridine and 23.3 g of 1-(4-piperidyl)-imidazolidin-2-one in 500 ml of isopropanol is stirred at 30° for 24 hours. Working up by a procedure analogous to that described in Example 1 yields, after the addition of acetone, 1-{1-[2-hydroxy-3-(3-methoxy-2-pyridyloxy)-propyl]-4-piperidyl}-imidazolidin-2-one with a melting point of 137°–142°. The compound forms a neutral fumarate, which after recrystallisation from a mixture of isopropanol and acetone melts, as the hydrate, at 124°–126°.

The starting material can be prepared as follows:

26.5 g of sodium hydride are added in the course of one hour to a mixture of 161 g of 3-methoxy-2-nitropyridine and 144 g of 2,2-dimethyl-5-hydroxymethyl-1,3-dioxolane in 1,000 ml of hexamethylphosphoric acid triamide, with stirring; by means of cooling, the temperature is kept at 0°–10° during the addition. The reaction mixture is then stirred for a further 5 hours with ice-cooling and then for 15 hours at room temperature. The reaction mixture is poured onto ice and extracted with diethyl ether. The organic extract is washed with a concentrated aqueous solution of sodium chloride, dried and evaporated. The residue is dissolved in 1,000 ml of ethanol, 100 ml of 2 N hydrochloric acid are added and the mixture is left to stand for 8 hours. After evaporating off the solvent, the residue is rendered alkaline with a concentrated solution of sodium hydroxide in water and extracted with ethyl acetate. Evaporating off the solvent yields a crude product from which crystalline 3-(3-methoxy-2-pyridyloxy)-1,2-propanediol with a melting point of 62°–65° is obtained on the addition of diethyl ether.

2 drops of trifluoroacetic acid are added to a solution of 62 g of 3-(3-methoxy-2-pyridyloxy)-1,2-propanediol in 350 ml of triethyl orthoacetate and the mixture is left to stand for 3 hours at 20°–30°. On evaporation, crude 2-ethoxy-5-(3-methoxy-2-pyridyloxymethyl)-2-methyl-1,3-dioxolane is obtained in the form of an oil, which is used without purification.

45 ml of trimethylchlorosilane are added to a mixture of 85 g of 2-ethoxy-5-(3-methoxy-2-pyridyloxymethyl)-2-methyl-1,3-dioxolane in 500 ml of methylene chloride and the mixture is stirred for one hour at 20°–30°. Complete evaporation under reduced pressure yields crude 2-(2-acetoxy-3-chloro-propoxy)-3-methoxy-pyridine in the form of an oil, which is used without purification.

A mixture of 80 g of 2-(2-acetoxy-3-chloropropoxy)-3-methoxy-pyridine, 900 ml of methylene chloride, 500 ml of a 2 N aqueous solution of sodium hydroxide and 9.5 g of tetrabutylammonium hydrogen sulphate is stirred vigorously for 16 hours at 20°–30°. The organic phase is then separated off and evaporated. The residual oil is dissolved in diethyl ether; the solution is filtered and the filtrate is treated with active charcoal and evaporated. This yields 2-(2,3-epoxy-propoxy)-3-methoxy-pyridine with a melting point of 63°–65°.

EXAMPLE 3

A mixture of 14.9 g of 2-chloro-3-(2,3-epoxypropoxy)-pyrazine (see, for example, German Offenlegungschrift No. 2,520,910) and 10.4 g of 1-(4-piperidyl-)imidazolidin-2-one in 150 ml of isopropanol is stirred for 24 hours at about 20°. A crystalline precipitate begins to separate out from the reaction mixture; in order to effect complete crystallisation a further 150 ml of diethyl ether are added. This yields 1-{1-[3-(3-chloro-2-pyrazinyloxy)-2-hydroxy-propyl]-4-piperidyl}-imidazolidin-2-one with a melting point of 150°–151°. The neutral fumarate prepared with the calculated amount of fumaric acid crystallises from a mixture of methanol and diethyl ether and melts at 172°–173°.

EXAMPLE 4

A mixture of 10.66 g of 1-{1-[3-(3-chloro-2-pyrazinyloxy)-2-hydroxy-propyl]-4-piperidyl}-imidazolidin-2-one and 1.78 g of sodium methylate in 150 ml of methanol is refluxed for 10 hours, with stirring. The reaction mixture is totally evaporated under a waterpump vacuum. The residue is dissolved in ethyl acetate and the solution is washed with water. The organic solution is dried over sodium sulphate and evaporated under a waterpump vacuum. This yields 1-{1-[2-hydroxy-3-(3-methoxy-2-pyrazinyloxy)-propyl]-4-piperidyl}-imidazolidin-2-one in the form of an oil. The hydrochloride prepared using a methanolic hydrochloric acid crystallises from a mixture of methanol and diethyl ether and melts at 222°–223° (with decomposition).

EXAMPLE 5

A mixture of 8.65 g of 2-methyl-3-(2,3-epoxypropoxy)-pyrazine (see, for example, German Offenlegungsschrift No. 2,520,910) and 6.75 g of 1-(4-piperidyl)-imidazolidin-2-one in 100 ml of isopropanol is stirred for 60 hours at about 20°. The reaction mixture is totally evaporated under a waterpump vacuum, the residue is dissolved in ethyl acetate and the solution is extracted with 2 N hydrochloric acid. The combined hydrochloric acid extracts are rendered alkaline with a concentrated aqueous solution of sodium hydroxide and extracted with methylene chloride. The combined organic extracts are washed with a little water, dried over sodium sulphate and evaporated under a waterpump vacuum. This yields oily 1-{1-[2-hydroxy-3-(3-methyl-2-pyrazinyloxy)-propyl]-4-piperidyl}-imidazolidin-2-one, which is converted to the neutral fumarate by treatment with the calculated amount of fumaric acid; the fumarate has a melting point of 168°–170° after recrystallisation from a mixture of methanol and acetone.

EXAMPLE 6

A mixture of 46.0 g of 3-(2,3-epoxy-propoxy)-2-nitropyridine and 35.0 g of 1-(4-piperidyl)-imidazolidin-2-one in 500 ml of isopropanol is refluxed for 2 hours. Working up analogously to Example 1 using methylene chloride as the extracting agent yields crude 1-{1-[2-hydroxy-3-(2-nitro-3-pyridyloxy)-propyl]-4-piperidyl}-imidazolidin-2-one, which after recrystallisation from isopropanol melts at 154°–158°.

In an analogous manner, 1-{1-[2-hydroxy-3-(2-nitro-3-pyridyloxy)-propyl]-4-piperidyl}-3-methyl-imidazolidin-2-one is obtained in the form of a yellow oil using 13.0 g of 3-(2,3-epoxy-propoxy)-2-nitropyridine and 11.0 g of 3-methyl-(4-piperidyl)-imidazolidin-2-one.

EXAMPLE 7

A mixture of 7.3 g of 1-chloro-3-(2-chloro-3-pyridyloxy)-2-propanol and 5.0 g of 3-methyl-1-(4-piperidyl)-imidazolidin-2-one is refluxed in 100 ml of isopropanol for 2 hours. Working up analogously to Example 1 yields oily 1-{1-[2-hydroxy-3-(2-chloro-3-pyridyloxy)-propyl]-4-piperidyl}-3-methyl-imidazolidin-2-one.

In an analogous manner, 1-{1-[2-hydroxy-3-(2-chloro-3-pyridyloxy)-propyl]-4-piperidyl}-imidazolidin-2-one with a melting point of 163°–166° is obtained using 1-(4-piperidyl)-imidazolidin-2-one.

The starting material is prepared as follows:

A mixture of 45 g of 2-chloro-3-pyridinol, 45 g of potassium carbonate, 150 ml of epichlorohydrin and 300 ml of acetone is refluxed for 5 hours. Filtering the mixture, evaporating the filtrate, dissolving the residue in ethyl acetate and washing the solution with water yields, after evaporating off the ethyl acetate, crude 1-chloro-3-(2-chloro-3-pyridyloxy)-2-propanol in the form of a dark brown oil which is purified by column chromatography on silica gel and elution with ether and then melts at 140°–143°.

EXAMPLE 8

1.1 g of 2-chloro-3-(2,3-epoxy-propoxy)-6-methylpyridine and 0.76 g of 1-(4-piperidyl)-imidazolidin-2-one are refluxed in 40 ml of isopropanol for 1 hour. Evaporating off the solvent and recrystallising the residue from the isopropanol/ether yields 1-{1-[2-hydroxy-3-(2-chloro-6-methyl-3-pyridyloxy)-propyl]-4-piperidyl}-imidazolidin-2-one with a melting point of 175°–180°.

The 2-chloro-3-(2,3-epoxy-propoxy)-6-methyl-pyridine used as the starting material is obtained by boiling 2-chloro-6-methyl-3-pyridinol with epichlorohydrin and potassium carbonate for 2 hours. It is further used in the form of the crude product.

EXAMPLE 9

2.5 g of 1-{1-[2-hydroxy-3-(2-benzyloxy-3-pyridyloxy)-propyl]-4-piperidyl}-imidazolidin-2-one are hydrogenated in 50 ml of methanol with the addition of 0.3 g of 5% Pd/C at atmospheric pressure and 20°–30° until the absorption of hydrogen has ceased. Filtering off the catalyst and evaporating the solution yields 3-{2-hydroxy-3-[4-(imidazolidin-2-on-1-yl)-1-piperidyl]-propoxy}-2-pyridine with a melting point of 217°–222°.

The starting material is obtained as follows:

(a) 3.6 g of a sodium hydride suspension (55%) are added in portions, at 0°–5°, to 15.7 g of 3-(2,3-epoxy-propoxy)-2-nitro-pyridine and 9.0 g of benzyl alcohol dissolved in 150 ml of 1,2-dimethoxyethane, with stirring and cooling, and the mixture is stirred for a further 3 hours at 0°–5° and for 2 hours at 20°–25°. The reaction mixture is evaporated, the residue is dissolved in ethyl acetate, the solution is washed with water and the ethyl acetate solution is evaporated. The residue (20 g) is chromatographed on 400 g of silica gel and eluted with toluene (250 ml fractions). 2-Benzyloxy-3-(2,3-epoxy-propoxy)-pyridine is obtained in the form of an oil from fractions 28–36.

(b) 4.8 g of 2-benzyloxy-3-(2,3-epoxypropoxy)-pyridine and 3.0 g of 1-(4-piperidyl)-imidazolidin-2-one are dissolved in 50 ml of isopropanol and the solution is stirred for 15–18 hours at 20–30°. The crystals which have precipitated out are filtered off with suction and washed with ether and yield 1-{1-[2-hydroxy-3-(2-benzyloxy-3-pyridyloxy)-propyl]-4-piperidyl}-imidazolidin-2-one with a melting point of 145°–147°.

EXAMPLE 10

A mixture of 7.1 g of 2-methyl-4-(2,3-epoxypropyl)-indole and 5.9 g of 1-(4-piperidyl)-2-imidazolidinone is dissolved in 125 ml of isopropyl alcohol and the solution is refluxed for 6 hours. The mixture is then cooled in an ice bath and filtered. The crystalline product is dissolved in isopropanol and recrystallised, if necessary with the addition of animal charcoal. 4-{3-[4-(2-Oxo-3-imidazolidinyl)-1-piperidyl]-2-hydroxy-1-propoxy}-2-methyl-1H-indole has a melting point of 208°–210°.

In an analogous manner, 4-{3-[4-(1-methyl-2-oxo-3-imidazolidinyl)-1-piperidyl]-2-hydroxy-1-propoxy}-2-methyl-1H-indole with a melting point of 184°–185° is prepared using 1-(4-piperidyl)-3-methyl-2-imidazolidinone.

In an analogous manner, 4-{3-[4-(2-oxo-benzimidazolidinyl)-piperidyl]-2-hydroxy-1-propoxy}-2-methyl-1H-indole with a melting point of 172°–174° is prepared using 1-(4-piperidyl)-2-benzimidazolinone.

The starting material is prepared as follows:

208 g of N-benzylpiperidone are hydrogenated with 8.5 g of N-methyl-ethylenediamine in 2,000 ml of methanol using 15 g of platinum-on-charcoal, the catalyst is filtered off and the filtrate is evaporated to dryness. Moisture still adhering to the residue is driven off with toluene. 173 g of the residue N'-(1-benzyl-4-piperidyl)-N"-methyl-ethylenediamine are introduced into a stirred flask together with 96.5 g of N,N-diisopropylethylamine in 3,000 ml of acetonitrile. 117.5 g of phenyl chloroformate are added dropwise to this mixture in the course of 30 minutes, at 0°–5°. A thick suspension forms and 96.5 g of N,N-diisopropylethylamine are added to this. The whole is then refluxed for 20 hours. It is then evaporated to dryness, all of the volatile constituents are driven off with toluene and the residue is taken up in 1,500 ml of ethyl acetate. The organic phase is extracted 6 times with, in each case, 500 ml of 2 N sodium hydroxide solution, dried and evaporated. 150 g of the residual oil are refluxed with 500 ml of alcohol and 150 ml of concentrated sodium hydroxide solution for 14 hours. The alcohol is then distilled off and the residue is partitioned between 1,000 ml of ethyl acetate and ice-water. The aqueous phase is separated off and the organic phase is extracted 4 times with, in each case, 250 ml of 2 N sodium hydroxide solution, dried and distilled. 1-(1-Benzyl-4-piperidyl)-3-methyl-2-imidazolidinone boils at 185°/0.18 mm.

127 g of the resulting product are debenzylated in 1,500 ml of methanol using 39 g of palladium-on-charcoal. The catalyst is filtered off, the filtrate is evaporated and the residue is distilled. 1-(4-Piperidyl)-3-methyl-2-imidazolidinone boils at 121°–124°/0.01 mm Hg and has a melting point of 76°–79°.

EXAMPLE 11

A mixture of 3.1 g of 2-methyl-4-(2,3-epoxypropyl)-indole and 3.4 g of 3-n-butyl-1-(4-piperidyl)-2-imidazolidinone is dissolved in 75 ml of isopropyl alcohol by warming slightly and the solution is stirred for 18 hours at room temperature. The resulting suspension is concentrated to about 40 ml under reduced pressure and cooled in an ice bath. The white crystalline product is filtered off and, after recrystallisation from isopropyl alcohol/diethyl ether, 4-{3-[4-(1-n-butyl-2-oxo-3-imidazolidinyl)-1-piperidyl]-2-hydroxy-1-propoxy}-2-methyl-1H-indole with a melting point of 116°–120° C. is obtained.

The 3-n-butyl-1-(4-piperidyl)-2-imidazolidinone used as the starting material can be prepared as follows:

20 ml of a 50% solution of benzyl chloroformate in toluene are added dropwise to a solution of 10.1 g of 1-(4-piperidyl)-imidazolidin-2-one and 6.06 g of triethylamine in 120 ml of methylene chloride, with stirring. The mixture is stirred for a further 2 hours at room temperature and the triethylamine hydrochloride which has precipitated out is then filtered off. The methylene chloride filtrate is washed twice with, in each case, 50 ml of water, dried with sodium sulphate and then evaporated. The residue is freed from the moisture which still adheres by treatment with toluene. After triturating with diethyl ether, 1-(1-carbobenzoxy-4-piperidyl)-imidazolidin-2-one with a melting point of 133°–135° C. is obtained in the form of a white crystalline product.

25 g of 1-(1-carbobenzoxy-4-piperidyl)-imidazolidin-2-one are added in portions to a mixture, which has been warmed to 80° C., of 2.4 g of sodium hydride in 100 ml of absolute dimethylformamide, with stirring. The mixture is stirred for a further 2 hours at 80° C. and 18.2 g of n-butyl iodide are then allowed to run in slowly dropwise (highly exothermic reaction). After stirring for a further 2 hours at 80° C., the reaction mixture is evaporated under reduced pressure and the residue is freed from dimethylformamide which is still adhering, by treatment with toluene. The reaction product is dissolved in 250 ml of ethyl acetate and the solution is washed twice with, in each case, 50 ml of water, dried over sodium sulphate and evaporated to dryness. The residue is chromatographed on 1.5 kg of silica gel using a mixture of chloroform/methyl alcohol (95:5) as the eluant mixture. In this way, 3-n-butyl-1-(1-carbobenzoxy-4-piperidyl)-imidazolidin-2-one is obtained in the form of a colourless oil.

A mixture of 43 g of 3-n-butyl-1-(1-carbobenzoxy-4-piperidy)-imidazolidin-2one, 100 ml of acetic acid and 89 ml of a 28% solution of hydrobromic acid in glacial acetic acid is stirred for 3 hours at a reaction temperature of 75° C. The mixture is then evaporated under reduced pressure and the residue is dissolved in 100 ml of water and extracted 3 times with, in each case, 100 ml of diethyl ether. The aqueous acid phase is rendered alkaline with 2 N sodium hydroxide solution and extracted 3 times with, in each case, 100 ml of chloroform. The combined chloroform extracts are dried over sodium sulphate and evaporated. The residual oil is subjected to fractional distillation in vacuo. This yields 3-n-butyl-1-(4-piperidyl)-imidazolidin-2-one with a boiling point of 155° under 0.1 mm Hg.

EXAMPLE 12

A mixture of 43 g of 3-n-butyl-1-1-carbobenzoxy-4-1H-indole and 3.2 g of 3-(2-hydroxy-ethyl)-1-(4-piperidyl)-2-imidazolidinone is dissolved in 75 ml of isopropyl alcohol by warming slightly and the solution is stirred for 18 hours at room temperature. This mixture is then evaporated to dryness under reduced pressure. After crystallising the residue from methylene chloride/diethyl ether, with the addition of active charcoal if necessary, 4-{3-[4-(1-hydroxyethyl-2-oxo-3-imidazolidinyl)-1-piperidyl}-2-hydroxy-1-propoxy}-2-methyl-1H-indole with a melting point of 158°–162° is obtained.

The 3-(2-hydroxyethyl)-1-(4-piperidyl)-imidazolidin-2-one used as the starting material can be prepared as follows:

20 ml of a 50% solution of benzyl chloroformate in toluene are added dropwise to a solution of 10.1 g of 1-(4-piperidyl)-imidazolidin-2-one and 6.06 g of triethylamine in 120 ml of methylene chloride, with stirring. The mixture is stirred for a further 2 hours at room temperature and the triethylamine hydrochloride which has precipitated out is then filtered off. The methylene chloride filtrate is washed twice with, in each case, 50 ml of water, dried over sodium sulphate and then evaporated. The residue is freed from moisture which is still adhering, by treatment with toluene. After triturating with diethyl ether, 1-(1-carbobenzoxy-4-piperidyl)-imidazolidin-2-one with a melting point of 133°–135° C. is obtained in the form of a white crystalline product.

A mixture of 1.35 g of sodium hydride in 70 ml of dimethylformamide and 14.2 g of 1-(1-carbobenzoxy-4-piperidyl)-imidazolidin-2-one is stirred at 80° C. for 4 hours. A solution of 11.7 g of 2-bromoethyl 2-tetrahydro-pyranyl ether in 30 ml of absolute dimethylformamide is then added dropwise in the course of 15 minutes. The mixture is stirred for a further 4 hours at 80° C. and is then evaporated under reduced pressure. The residue is freed from dimethylformamide which is still adhering, by treatment with toluene. The reaction product is dissolved in ethyl acetate, the solution is washed twice with, in each case, 50 ml of water and the ethyl acetate phase is dried over sodium sulphate and evaporated. The residual oil is chromatographed on 1.5 g of silica gel using a mixture of chloroform/methyl alcohol (95:5) as the eluant mixture. In this way, 1-(1-carbobenzoxy-4-piperidyl)-3-[2-(2-tetrahydropyranyloxy)-ethyl]-imidazolidin-2-one is obtained in the form of a slightly yellowish oil.

A solution of 59.7 g of 1-(1-carbobenzoxy-4-piperidyl)-3-[2(2-tetrahydropyranyloxy)-ethyl]-imidazolidin-2-one in 1,200 ml of absolute methanol is hydrogenated at room temperature and normal pressure with the addition of 1 mol equivalent of hydrochloric acid and 6 g of palladium-on-charcoal catalyst until 2 mol equivalents of hydrogen have been taken up. The catalyst is then filtered off and the filtrate is evaporated under reduced pressure. The residue is freed from moisture which is still adhering, by treatment with toluene. The reaction product is chromatographed on 2 kg of basic aluminium oxide using a mixture of chloroform-/methanol (85:15) as the eluant mixture. In this way, 3-(2-hydroxyethyl)-1-(4-piperidyl)-imidazolidin-2-one is obtained in the form of a viscous oil, which is further used without additional purification.

EXAMPLE 13

A mixture of 4.1 g of 2-methyl-4-(2,3-epoxy-propyl)-1H-indole and 5.2 g of 3-benzyl-1-(4-piperidyl)-2-imidazolidinone is dissolved in 100 ml of isopropyl alcohol by warming slightly and the solution is stirred for 24 hours at room temperature. The mixture is then cooled in an ice bath and the precipitate is filtered off. The crystalline product is dissolved in isopropyl alcohol and recrystallised, if necessary with the addition of animal charcoal. 4-{3-[4-(1-Benzyl-2-oxo-3-imidazolidinyl)-1-piperidyl]-2-hydroxy-1-propoxy}-2-methyl-1H-indole has a melting point of 97°–100° C.

The 1-benzyl-3-(4-piperidyl)-imidazolidin-2-one used as the starting material can be prepared as follows.

A mixture of 42.8 g of benzylamine and 120 ml of methyl ethyl ketone is initially introduced, with stirring and cooling with an ice bath. 41 g of 2-bromo-ethylamine hydrobromide are added in portions to this mixture and the resulting mixture is refluxed for 16 hours. The mixture is then cooled in an ice bath and the precipitate which has formed is filtered off. The crystalline product is dissolved in 150 ml of water and washed twice with, in each case, 50 ml of diethyl ether. The aqueous phase is rendered alkaline with concentrated ammonia solution and extracted four times with, in each case, 100 ml of chloroform. The combined chloroform extracts are dried and evaporated to dryness under reduced pressure. The residue is freed from moisture which is still adhering, by treatment with toluene. After fractional distillation of the residue under a high vacuum, 1-benzyl-ethylenediamine with a boiling point of 88°–90° C. under 0.02 mm Hg is obtained.

A solution of 29.25 g of 1-benzyl-ethylenediamine and 36.85 of 1-benzyl-4-piperidone in 100 ml of absolute methyl alcohol is hydrogenated at room temperature and normal pressure with the addition of 2 g of a 5% platinum-on-charcoal catalyst and 0.49 g of concentrated chemically pure sulphuric acid until 1 mol equivalent of hydrogen has been taken up. The catalyst is then filtered off and the filtrate is evaporated to dryness. The residue is dissolved in 2 N hydrochloric acid and extracted three times with, in each case, 75 ml of diethyl ether. The acid aqueous phase is rendered alkaline with concentrated ammonia solution and extracted five times with, in each case, 75 ml of chloroform. The combined chloroform phases are dried over sodium sulphate and evaporated to dryness under reduced pressure. The residue is freed from moisture which is still adhering, by treatment with toluene, and in this way 1-benzyl-4-(2-benzylamino-ethylamino)-piperidine is obtained in the form of an oily residue, which is further used without further purification.

13.7 g of the crude 1-benzyl-4-(2-benzylamino-ethylamino)-piperidine are initially introduced into a stirred flask with 5.5 g of N,N-diisopropylamine in 170 ml of acetonitrile. 7.3 g of phenyl chloroformate are added dropwise at 0°–5° C. in the course of 30 minutes. A thick suspension forms and 5.5 g of N,N-diisopropylethylamine are added to this. The mixture is then refluxed for 18 hours. The mixture is then evaporated under reduced pressure and all of the volatile constituents are then driven off with toluene. The residue is dissolved in 150 ml of ethyl acetate and the solution is extracted four times with, in each case, 50 ml of 2 N sodium hydroxide solution. The organic phase is dried and evaporated. The residual oil is refluxed with 60 ml of ethyl alcohol and 25 ml of concentrated sodium hydroxide solution for 15 hours. The alcohol is then distilled off and the residue is partitioned between 100 ml of ethyl acetate and ice-water. The aqueous phase is separated off and the organic phase is extracted three times with, in each case, 30 ml of 2 N sodium hydroxide solution. The ethyl acetate phase is then dried and evaporated. The residue is chromatographed on 500 g of silica gel using a mixture of chloroform/methyl alcohol (9:1) as the eluant mixture. This yields 1-benzyl-3-(1-benzyl-4-piperidyl)-imidazolidin-2-one.

A mixture of 12 g of 1-benzyl-3-(1-benzyl-4-piperidyl)-imidazolidin-2-one, 120 ml of a 70% aqueous solution of methyl alcohol and 3.39 g of concentrated chemically pure hydrochloric acid is hydrogenated at room temperature and normal pressure with the addition of 2.4 g of a 5% palladium-on-charcoal catalyst until 1 mol equivalent of hydrogen has been taken up. The catalyst is then filtered off and the filtrate is evaporated under reduced pressure. The residue is rendered alkaline with concentrated aqueous ammonia solution and extracted five times with, in each case, 50 ml of chloroform. The combined chloroform extracts are dried and evaporated under reduced pressure. The residual crystalline product is partitioned in a mixture of diethyl ether/petroleum ether, filtered off and dried. This yields 1-benzyl-3-(4-piperidyl)-imidazolidin-2-one with a melting point of 110°–113° C.

EXAMPLE 14

A mixture of 2.65 g of 2-phenyl-4-(2,3-epoxypropyl)-indole and 2.0 g of 1-(4-piperidyl)-2-imidazolidinone is stirred in 100 ml of isopropanol for 24 hours at room temperature. The small amount of resin which has precipitated is then separated off, the filtrate is evaporated and the residue is treated in methanol with animal charcoal. The mixture is filtered, the filtrate is evaporated and the residue is recrystallised from 1:4 isopropyl alcohol/ethyl acetate. 4-{3-[4-(2-Oxo-3-imidazolidinyl)-1-piperidyl]-2hydroxy-1-propoxy}-2-phenyl-1H-indole has a melting point of 166°–168° C.

The starting material is prepared as follows:

23.0 g of 2-phenyl-4-hydroxy-indole are introduced into a solution of 5.2 g of sodium hydroxide solution in 250 ml of water and the suspension is stirred with 17.2 g of epibromohydrin for 24 hours at room temperature. The grey resin which has precipitated is filtered off and dissolved in chloroform, the solution is dried and evaporated and the residue is freed from epibromohydrin which is still adhering, in a bulb tube at 100°/12 mm Hg. The residual oil is chromatographed in 98:2 chloroform/methanol on silica gel. 2-Phenyl-4-(2,3-epoxypropyl)-indole is recrystallised from isopropyl alcohol/petroleum ether and has a melting point of 89°–90° C.

The 2-phenyl-4-hydroxy-indole was synthesised from 4-oxo-2-phenyl-4,5,6,7-tetrahydroindole by aromatisation with palladium-on-charcoal in diphenyl ether and has a melting point of 120°–123° C.

EXAMPLE 15

4.5 g of 1-{3-[(2methyl-4-indolyloxy)-2-hydroxy-1-propyl]}-4-(2-oxo-3-imidazolidinyl)-pyridinium bromide are hydrogenated at 40° in a mixture of 25 ml of water and 25 ml of ethanol with 2.0 g of platinum dioxide. The catalyst is then filtered off and the filtrate is evaporated in vacuo. 2 N Sodium hydroxide solution is added to the residue and the alkaline phase is extracted with ethyl acetate. This extract is dried and evaporated. The residue is recrystallised from isopropanol with the addition of animal charcoal. 4-{3-[4-(2-Oxo-3-imidazolidinyl)-1-piperidyl]-2-hydroxy-1-propoxy}-2-methyl-1H-indole has a melting point of 208°–210° C.

The quaternary starting material is prepared by heating 3-(2-methyl-4-indolyloxy)-2-hydroxy-1-bromopropane with 1-(4-pyridyl)-2-imidazolidinone in dimethylformamide at 100°.

EXAMPLE 16

34.6 g of 1-{3-[(2-methyl-4-indolyloxy)-2-hydroxy-1-propyl]}-4-(2-amino-ethylamino)-piperidine are initially introduced into a stirred flask together with 13.0 g of N,N-diisopropylethylamine in 350 ml of acetonitrile. 15.6 g of phenyl chloroformate are added dropwise to this mixture at 0°–5° C. in the course of 30 minutes. A thick suspension forms and 13.0 g of N,N-diisopropylethylamine are added to this. The mixture is then refluxed for 18 hours and is then evaporated in vacuo and all of the volatile constituents are then driven off with toluene. The residue is dissolved in 300 ml of ethyl acetate and this solution is extracted four times with, in each case, 100 ml of 2 N sodium hydroxide solution. The organic phase is dried and evaporated. The residual oil is refluxed with 120 ml of ethanol and 50 ml of concentrated sodium hydroxide solution for 15 hours. The alcohol is then distilled off and the residue is partitioned between 200 ml of ethyl acetate and ice-water. The aqueous phase is separated off and the organic phase is extracted three times with, in each case, 60 ml of 2 N sodium hydroxide solution. The ethyl acetate phase is then dried and evaporated. The residue is recrystallised from isopropanol with the addition of animal charcoal. 4-{3-[4-(2-Oxo-3-imidazolidinyl)-1-piperidyl]-2-hydroxy-1-propoxy}-2-methyl-1H-indole has a melting point of 208°–210°.

The starting material is prepared by reductive alkylation of 1-[3-(2-methyl-4-indolyloxy)-2-hydroxy-1-propyl]-4-piperidone with ethylenediamine under palladium-on-charcoal catalysis.

EXAMPLE 17

Tablets containing 20 mg of 4-{3-[4-(2-oxo-3-imidazolidinyl)-1-piperidyl]-2-hydroxyl-1-propoxy}-2-methyl-1H-indole hydrochloride can be prepared, for example, as follows:

| Composition (for 5,000 tablets) | |
|---|---|
| 4-{3-[4-(2-oxo-3-imidazolidinyl)-1-piperidyl]-2-hydroxy-1-propoxy}-2-methyl-1H-indole hydrochloride | 100 g |
| lactose | 150 g |
| corn starch | 150 g |
| colloidal silica | 25 g |
| talc | 25 g |
| magnesium stearate | 5 g |
| water | q.s. |

The 4-{3-[4-(2-oxo-3-imidazolidinyl)-piperidyl]-2-hydroxy-1-propoxy}-2-methyl-1H-indole hydrochloride is mixed with the lactose, the colloidal silica and a portion of the corn starch and the mixture is forced through a sieve. A further portion of the corn starch is mixed to a paste with five times the amount of water on a waterbath and the powder mixture is thoroughly kneaded with this paste until a slightly plastic mass forms. The mass is forced through a sieve and dried and the dry granules are again sieved. The remainder of the corn starch, the talc and the magnesium stearate are then mixed in and the mixture is compressed to tablets (with a breaking notch) weighing 0.1 g.

What is claimed is:

1. A piperidino propanol of the formula

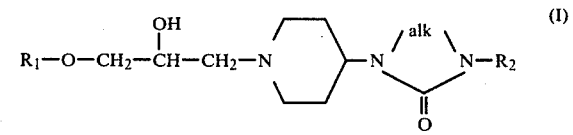

wherein $R_1$ is 2-pyrazinyl, pyridyl or indolyl, which is unsubstituted or substituted by lower alkyl, lower alkoxy, lower alkylthio, halogen with an atomic number of not more than 35 or nitro, $R_2$ is hydrogen, lower alkyl, cycloalkyl having 3 to 8 carbon atoms or phenyl-lower alkyl which is unsubstituted or substituted in the phenyl moiety by lower alkyl, lower alkoxy or halogen with an atomic number of not more than 35, and alk is lower alkylene have 2-3 carbon atoms, which separates the two nitrogen atoms by 2-3 carbon atoms, and a pharmaceutically acceptable acid addition salt thereof.

2. Piperidino propanols according to claim 1, wherein $R_1$ is 2-pyrazinyl, pyridyl or indolyl, which is unsubstituted or substituted by lower alkyl, lower alkoxy, lower alkylthio, halogen with an atomic number of not more than 35 and/or nitro, $R_2$ is hydrogen, lower alkyl or phenyl-lower alkyl and alk is lower alkylene having 2-3 carbon atoms, which separates the two nitrogen atoms by 2-3 carbon atoms, and a pharmaceutically acceptable acid addition salt thereof.

3. Piperidino propanols according to claim 1, wherein $R_1$ is 4-indolyl, 2-pyrazinyl or pyridyl, which in the ortho-position relative to the linking carbon atom and/or nitrogen atom can be substituted by lower alkyl, lower alkoxy, lower alkylthio, halogen with an atomic number of not more than 35 or nitro, and can contain further substituents of this type, $R_2$ is hydrogen, lower alkyl or phenyl-lower alkyl and alk is ethylene, and a pharmaceutically acceptable acid addition salt thereof.

4. Piperidino propanols according to claim 1, wherein $R_1$ is 2-pyrazinyl which is unsubstituted or substituted in the 3-position by lower alkyl, lower alkoxy, lower alkylthio, halogen with an atomic number of not more than 35 or nitro, $R_2$ is hydrogen or lower alkyl and alk is ethylene, and a pharmaceutically acceptable acid addition salt thereof.

5. A compound according to claim 1, which is 1-{1-[2-hydroxy-3-(3-methoxy-2-pyrazinyloxy)-propyl]-4-piperidyl}-imidazolidin-2-one and its pharmaceutically acceptable acid addition salts.

6. A compound according to claim 1, which 4-{3-[4-(2-oxo-3-imidazolidinyl)-1-piperidyl]-2-hydroxy-1-propoxy}-2-methyl-1H-indole and its pharmaceutically acceptable acid addition salts.

7. A compound according to claim 1, which is 4-{3-[4-(1-methyl-2-oxo-3-imidazolidinyl)-1-piperidyl]-2-hydroxy-1-propoxy}-2-methyl-1H-indole and its pharmaceutically acceptable acid addition salts.

8. A pharmaceutical composition useful in the treatment of hypertension in a warmblooded animal comprising a therapeutically effective amount of a compound according to claim 1 or of a pharmaceutically acceptable acid addition salt thereof with a pharmaceutical carrier.

9. A pharmaceutical composition according to claim 8, which contains 1-{1-[2-hydroxy-3-(3-methoxy-2-pyrazinyloxy)-propyl]-4-piperidyl}-imidazolidin-2-one or a pharmaceutically acceptable acid addition salt thereof.

10. A pharmaceutical composition according to claim 8, which contains 4-{3-[4-(2-oxo-3-imidazolidinyl)-1-piperidyl]-2-hydroxy-1-propoxy}-2-methyl-1H-indole or a pharmaceutically acceptable acid addition salt thereof.

11. A pharmaceutical composition according to claim 8, which contains 4-{3-[4-(1-methyl-2-oxo-3-imidazolidinyl)-1-piperidyl]-2-hydroxy-1-propoxy}-2-methyl-1H-indole or a pharmaceutically acceptable acid addition salt thereof.

12. A method of treating hypertension in a warmblooded animal which comprises administering to said animal a therapeutically effective amount of a compound according to claim 1, or a pharmaceutically acceptable acid addition salt thereof.

13. A method according to claim 12, which comprises administering a therapeutically effective amount of 1-{1-[2-hydroxy-3-(3-methoxy-2-pyrazinyloxy)-propyl]-4-piperidyl}-imidazoldidin-2-one, or a pharmaceutically acceptable acid addition salt thereof.

14. A method according to claim 12, which comprises administering a therapeutically effective amount of 4-{3-[4-(2-oxo-3-imidazolidinyl)-1-piperidyl]-2-hydroxy-1-propoxy}-2-methyl-1H-indole, or a pharmaceutically acceptable acid addition salt thereof.

15. A method according to claim 12, which comprises administering a therapeutically effective amount of 4-{3-[4-(1-methyl-2-oxo-3-imidazolidinyl)-1-piperidyl]-2-hydroxy-1-propoxy}-2-methyl-1H-indole, or a pharmaceutically acceptable acid addition salt thereof.

* * * * *